US008541329B2

(12) United States Patent
Ritzberger et al.

(10) Patent No.: US 8,541,329 B2
(45) Date of Patent: Sep. 24, 2013

(54) PROCESS FOR THE PREPARATION OF COLOURED BLANKS AND DENTAL SHAPED PARTS

(75) Inventors: Christian Ritzberger, Nenzing (AT); Elke Apel, Oberschan (CH); Wolfram Höland, Schaan (LI); Frank Rothbrust, Frastanz (AT); Harald Kerschbaumer, Klaus (AT); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 13/224,492

(22) Filed: Sep. 2, 2011

(65) Prior Publication Data

US 2011/0319254 A1 Dec. 29, 2011

Related U.S. Application Data

(62) Division of application No. 11/802,053, filed on May 18, 2007, now Pat. No. 8,034,264.

(30) Foreign Application Priority Data

May 23, 2006 (DE) .......................... 10 2006 024 065
Sep. 13, 2006 (EP) ...................................... 06120608
Mar. 8, 2007 (EP) ...................................... 07004776

(51) Int. Cl.
*C04B 35/48* (2006.01)
*C04B 35/00* (2006.01)
*C09K 3/00* (2006.01)

(52) U.S. Cl.
USPC .............. 501/103; 501/102; 501/126; 106/35

(58) Field of Classification Search
USPC ................. 501/102, 103, 104, 105, 126, 127, 501/128, 129, 130, 131, 132; 106/35
See application file for complete search history.

(56) References Cited

U.S. PATENT DOCUMENTS

| | | | |
|---|---|---|---|
| 3,984,524 A | 10/1976 | Alexandrov et al. | |
| 4,170,823 A * | 10/1979 | Smyth et al. | 433/202.1 |
| 4,742,030 A | 5/1988 | Masaki | |
| 4,940,523 A | 7/1990 | Takeshima | |
| 5,011,403 A | 4/1991 | Sadoun et al. | |
| 5,043,316 A | 8/1991 | Janssens | |
| 5,059,562 A | 10/1991 | Gentsu | |
| 5,219,805 A * | 6/1993 | Yoshida et al. | 501/103 |
| 5,263,858 A | 11/1993 | Yoshida et al. | |
| 5,308,243 A | 5/1994 | Emmons | |
| 5,656,564 A | 8/1997 | Nakayama et al. | |
| 5,800,164 A | 9/1998 | Pfau | |
| 6,030,209 A | 2/2000 | Panzera | |
| 6,254,757 B1 | 7/2001 | Lashmore et al. | |
| 6,379,593 B1 | 4/2002 | Datzmann et al. | |
| 6,495,072 B1 | 12/2002 | Van der Zel | |
| 6,709,694 B1 | 3/2004 | Suttor | |
| 6,713,421 B1 * | 3/2004 | Hauptmann et al. | 501/103 |
| 7,011,522 B2 | 3/2006 | Panzera et al. | |
| 7,686,989 B2 | 3/2010 | Van der Zel | |
| 2002/0127130 A1 | 9/2002 | Lashmore et al. | |
| 2003/0125189 A1 | 7/2003 | Castro et al. | |
| 2004/0152034 A1 | 8/2004 | Cummings et al. | |
| 2005/0023710 A1 | 2/2005 | Brodkin et al. | |
| 2005/0136096 A1 | 6/2005 | Davidson | |
| 2007/0187185 A1 | 8/2007 | Abraham et al. | |
| 2008/0206460 A1 | 8/2008 | Rhoades | |

FOREIGN PATENT DOCUMENTS

| | | |
|---|---|---|
| DE | 3418987 | 11/1985 |
| DE | 19904522 | 8/2000 |
| DE | 19714178 | 9/2003 |
| EP | 0218853 | 4/1987 |
| EP | 0 378 414 | 7/1990 |
| EP | 0442150 | 8/1991 |
| EP | 0955267 | 9/2003 |
| EP | 1076036 | 10/2003 |
| EP | 1354567 | 10/2003 |
| EP | 1400232 | 3/2004 |
| EP | 1210054 | 8/2004 |
| FR | 2781366 | 1/2000 |
| JP | 2145475 | 6/1990 |
| JP | 2145476 | 6/1990 |
| JP | 3028161 | 2/1991 |
| JP | 5043316 | 2/1993 |
| JP | 8033650 | 6/1996 |
| JP | 2005289721 | 10/2005 |
| WO | 02085242 | 10/2002 |
| WO | 2007053084 | 5/2007 |

OTHER PUBLICATIONS

P. Duran, P. Recio, J.R. Jurado, C. Pascual and C. Moure, Preparation, Sintering, and Properties of Translucent Er2O3—Doped Tetragonal Zirconia, J. Am. Ceram. Soc., vol. 72, No. 11, pp. 2088-2093, 1989.

(Continued)

*Primary Examiner* — Kaj Olsen
*Assistant Examiner* — Noah Wiese
(74) *Attorney, Agent, or Firm* — Ann M. Knab; Thad McMurray

(57) ABSTRACT

The invention relates to compositions based on $ZrO_2$, and single- and multi-coloured blanks made from oxide ceramics, and a process for their preparation, in which a) oxide ceramic powder is coated with a colouring substance, b) the coated powders are preferably graded and at least one coloured powder is filled into a compression mould, c) the coloured powder or powders are compressed to produce a shaped body, and d) the compressed shaped body is sintered to produce a blank, and to the use of these blanks for the preparation of dental restorations.

39 Claims, No Drawings

(56) References Cited

OTHER PUBLICATIONS

M. Yashima, T. Nagotome, T. Noma, N. Ishizawa, Y. Suzuki and M. Yoshimura, "Effect of Dopant Species on Tetragonal to Monoclinic Phase Transformation of Arc-Melted ZrO2-RO15 (R=Sm, Y, Er, and Sc) in Water . . . " J. Am. Ceram. Soc., No. 78, No. 8, pp. 2229-2293, 1989.

K.C. Shah, I. Dnery and J.A. Holloway, "Physical Properties of Cerium-Doped Tetragonal Zirconia", Abstract 0080, Journal of Dental Research, Vo. 85, Special Issue A, 2006.

Xie, Zhipeng et al., Microwave processing and properties of Ce-Y-ZrO2 ceramics with 2.45 GHz irradiation, 1999, Materials Letters, 38, pp. 190-196.

\* cited by examiner

PROCESS FOR THE PREPARATION OF COLOURED BLANKS AND DENTAL SHAPED PARTS

CROSS-REFERENCE TO RELATED APPLICATIONS

This application is a divisional application of U.S. application Ser. No. 11/802,053, filed May 18, 2007, which claims priority pursuant to 35 U.S.C. §119, to German Patent Application No. 10 2006 024 065.0 filed May 23, 2006, and European Patent Application Nos. 06120608.2 filed Sep. 13, 2006, and 07004776.6 filed Mar. 8, 2007, all of which are hereby incorporated by reference

FIELD

The present invention relates to single- or multi-coloured shaped bodies, blanks and dental shaped parts made from oxide ceramics, a process for their preparation, their use for the preparation of dental restoration shaped parts and also a composition which is particularly suitable for their manufacture.

BACKGROUND

In the discussion that follows, reference is made to certain structures and/or methods. However, the following references should not be construed as an admission that these structures and/or methods constitute prior art. Applicants expressly reserve the right to demonstrate that such structures and/or methods do not qualify as prior art.

The use of oxide ceramics as a framework material for dental restorations has long been state of the art. This material is characterized by an excellent biocompatibility and outstanding mechanical properties. For many years it has also been widely used as an implant material and for prostheses. In the past few years, ceramics based on partially stabilized $ZrO_2$ ceramics have been used in particular.

The shaping of these ceramics in dental engineering is typically performed by mechanical means. In particular, milling of partially sintered ceramics with CAD/CAM processing units has gained acceptance. The shrinkage which occurs during final densification of shaped bodies, going from a density of approximately 40-60% to a density of more than 95% is taken into account during the mechanical processing. The quoted density is relative to the respective theoretical density.

The disadvantage of the $ZrO_2$ ceramics is the low translucency and their milky-white colour. A non-coloured and non-coated restoration or restoration part looks like an unnatural tooth. Colouring the $ZrO_2$ ceramic to match the patient's situation for an aesthetic tooth reconstruction is thus essential.

A particularly great disadvantage of sintered ceramics according to the state of the art is that they do not produce blanks for CAD/CAM processing in open-pored form or in dense-sintered form which are multi-coloured or have zones of different colours corresponding to the coloration of a natural tooth.

All that is known from the state of the art is a series of technical solutions for coloured, not multi-coloured, blanks. However, these solutions have the disadvantage that the natural tooth colour, the colour gradient, the polychromatism, the graduated translucency and brightness of colour were not achieved. These known solutions are described as follows:

The preparation of an open-porous coloured and white $Y_2O_3$-containing $ZrO_2$ blank is achieved according to EP 1 210 054 from liquids via co-precipitation from chlorides which contain Zr, Y, Al, Ga, Ge, In, Fe, Er and Mn ions. By means of the co-precipitation and subsequent calcination, the prepared powder already contains the colouring ions before shaping. Oxides from the group $Fe_2O_3$, $Er_2O_3$ and $MnO_2$ are selected as colouring compounds. The disadvantage of this invention is that a very costly and laborious method of the co-precipitation process with subsequent calcination must be carried out in order to obtain a coloured powder. This means that this must be carried out for every single colour.

In the following disclosures monolithic ceramics are presented which each allow one specific colour, thus no polychromatism, to be achieved:

U.S. Pat. No. 5,263,858 (Yoshida et el.) describes the preparation of ivory-coloured shaped bodies for dental applications (brackets), wherein during the preparation of the stabilized $ZrO_2$ ceramic colouring compounds in solutions are added before the calcination or powdery mixtures of colouring oxides after the calcination. In order to achieve the desired ivory shade, the addition of $Fe_2O_3$, $Pr_6O_{11}$ and $Er_2O_3$ is necessary. However, this process has the disadvantage that it is a multi-stage process.

It is further known from the state of the art according to FR 2 781 366 to mix the colouring components with the starting powder of the $ZrO_2$, grind and sinter jointly. $Fe_2O_3$, $CeO_2$ and $Bi_2O_3$ are mentioned as colouring oxides.

EP 0 955 267 mentions contents of 5-49 wt.-% $CeO_2$, whereby a colouring is achieved.

For the preparation of completely cubically stabilized zirconium dioxide in the arc-furnace process, according to EP 1 076 036 B1 one or more stabilizing and colouring oxides or their precursors are added to a $ZrO_2$ source. The colouring oxides of the elements Pr, Ce, Sm, Cd, Tb are inserted into the crystal lattice of the $ZrO_2$ after the sintering process.

U.S. Pat. No. 5,656,564 relates to the preparation of zirconium oxide shaped bodies which contain oxides of the rare earths boron oxide, aluminium oxide and/or silicon oxide. The shaped bodies contain the zirconium dioxide as a mixed phase of tetragonal and monoclinal $ZrO_2$. Oxides of the elements Pr, Er and Yb are introduced into the sintered ceramic as colouring oxides.

Technical solutions are further known according to the state of the art which allow coloured blanks to be obtained by infiltration of liquids. However, these technical solutions have the serious drawback that a colouring takes place after the pre-sintering process and thus liquids are introduced into an open-porous ceramic body. The colouring is thus not completely homogeneous and also a multi-coloration cannot be achieved.

Unlike sintered ceramics, such as $ZrO_2$ and $Al_2O_3$, a process for the preparation of multi-coloured glass ceramic blanks is known in the materials group of the glass ceramics (DE 197 14 178 C2). However, the preparation of multi-coloured $ZrO_2$ blanks is not mentioned in this invention.

A disadvantage of the known solutions from the state of the art is that multi-coloured sintered ceramic blanks cannot be prepared. Moreover, the solutions according to the state of the art are very costly and quality problems arise. The latter applies e.g. to the infiltration technique, in which due to the subsequent colouring of a partially sintered blank or of a shaped dental product only the voids (pores) between the partially sintered particles of the starting powder can be occupied by the colouring ions. As a result, also only discrete areas of the surface of the particles are coloured with a layer of the colouring oxides, a continuous coverage of the surface of the particles of the starting powder not being possible. A further great disadvantage with an infiltration is the concentration gradient of the colouring from the outside inwards. If a porous body is introduced into the colouring solution, the starting solution releases part of the dissolved colouring ions, starting from the outside inwards, and thus the colouring solution is "depleted" of some of its colouring substances. The consequence of this is that there is a higher concentration of the colouring ions or then oxides outside than in the inside of the shaped body. Furthermore, only a certain depth of penetration can be achieved by means of the infiltration technique.

SUMMARY

The object of the invention is to avoid the disadvantages of the state of the art described above and to prepare an oxide powder that contains the colouring compounds uniformly distributed and is suitable for further processing to a dental restoration part from this uniformly coloured oxide powder, as well as a shaped body, an open-pored blank and a dental shaped part, which contain the colouring compounds uniformly distributed therein.

A further object of the invention is to provide single- or multi-coloured shaped parts, blanks and dental shaped parts which contain the colouring compounds in a gradient or zonal structure.

The first object of the invention is achieved by processes in which
a) an oxide powder is coated with a colouring substance,
b) the coated powder is optionally graded and optionally filled into a compression mould,
c) the coloured powder is compressed to give a shaped body and
d) the compressed shaped body is sintered to produce a blank, and
e) optionally the dental shaped part is formed therefrom.

The further object of the invention is achieved by single- and multi-coloured shaped bodies, blanks and dental shaped parts, made from coloured oxide ceramic powder or from coloured oxide ceramic powder and uncoloured oxide ceramic powder, which have a ratio of the oxide ceramic component to the colouring oxide or of the mixtures of colouring oxides in parts by weight of 100:0.0001 to 2.0.

As used herein, "layer" means an individual component which produces a single-coloured shaped body, blank or dental shaped part. The term "layers" illustrates the course of the colour as a colour gradient or zones of a multi-coloured shaped body, blank or multi-coloured dental shaped part.

The invention also relates to the use of the single- or multi-coloured shaped body, blank or dental shaped part for the preparation of dental restoration parts.

The invention furthermore relates to a composition based on $ZrO_2$ which already with very small quantities of colouring substances can be processed to produce dental restorations closely resembling the natural teeth.

DETAILED DESCRIPTION

With the processes according to the invention, the colouring of the oxide ceramic takes place before the compression of the blanks and thus before the pre-sintering or sintering process. For the preparation of multi-coloured shaped bodies, blanks or dental shaped parts, the coating can be carried out with further colouring substances. For this, in a first step a first colouring substance is applied on an uncoloured oxide ceramic powder. In a second step, the next colouring substance is then applied on further uncoloured oxide ceramic powders. Depending on the number of desired colours, in several further steps a further colouring, with further colouring substances applied on further uncoloured oxide ceramic powders, can take place. The result is therefore oxide powder particles containing different colour compounds.

Coating with the colouring substances can be carried out in a fluidized-bed reactor. Other coating methods known to a person skilled in the art can also be used according to the invention.

Suitable fluidized-bed methods are known from other fields of the art. These methods have not yet been used for the colouring of oxide ceramic powders which are used in the dental field.

A material, loosened by a carrier medium (gas or liquid), of fine-grained solid particles is moved in the fluidized bed (also called fluid bed). For this, a gas flows from bottom to top through a stationary packing comprising oxide ceramic powder with an average grain diameter of the granules of 1 to 100 μm, preferably 30 to 80 μm. At a specific rate of flow (loosening point, fluidizing point) the packing transforms into the fluidized bed. Powders with the given average granule diameter are therefore preferred. Either the bottom spray or the top spray method can be used during the fluidized coating.

As the fluidized bed forms the weight force of the solid particles is neutralized by the oppositely-directed flow force of the carrier medium. The solid then behaves similarly to a liquid, i.e. it can be easily supplied or removed during the operation. A very intensive material and heat exchange takes place in the fluidized bed. Consequently, a colouring of the oxide ceramic powders can be achieved according to the invention by using a fluid which contains colouring substances.

Oxidic sintered ceramics, such as $ZrO_2$ powders, can be used as oxide ceramic powders.

As used herein, "sintered ceramics" means products which are produced from crystalline raw materials in a heat treatment process by sintering, wherein the crystal portion is very largely retained and only a small portion, in most cases well below 5 vol-% glass phase portion, forms between the individual crystals.

According to the invention the $ZrO_2$ can also be doped with further metal oxides. For example a doping with $CeO_2$, $Y_2O_3$, MgO or CaO is possible. $HfO_2$ and $Al_2O_3$ can also be contained in the $ZrO_2$ powder.

The oxides of the d- and f-elements of the periodic table of the elements can be used as colouring oxides. The colouring oxides $Pr_2O_3$, $Fe_2O_3$, $Tb_2O_3$ and/or $Cr_2O_3$ and further oxides are preferably used for this.

$Pr_2O_3$, $Fe_2O_3$ and $Tb_2O_3$ are used as colouring oxides according to certain aspects of the invention.

Oxides of the elements Mn, V, Ti, Nd, Eu, Dy, Er and/or Yb, in particular oxides of Mn, can be used as further colouring oxides.

Aqueous solutions of various salts can preferably be used as colouring substances. Water-soluble salts of d- or f-elements of the periodic table can be utilized. Nitrate or chloride hydrates of these elements are particular examples. Examples of salts that can be used are $Pr(NO_3)_3 \cdot 5H_2O$, $Fe(NO_3)_3 \cdot 9H_2O$ or $Tb(NO_3)_3 \cdot 5H_2O$.

In addition to the colouring substances, suitable water-soluble binders can also be used as compression aids for the powder. The binders can be dissolved with the above-mentioned salts in water and homogenized. Polyvinyl alcohol is particularly preferred as a binder.

According to further embodiments a surfactant can be added to the powder, as this surprisingly improves compressibility. This is shown by a higher compression density at the same pressure. Non-ionic or amphoteric surfactants, such as polyglycol ethers or alkyl sulphonates, can be utilized.

The oxide ceramic powders coated with the colouring substances are preferably graded, e.g. screened using sieves with a mesh width of <90 μm, in a second step. Grading may be performed when there is agglomeration of the powder.

The optionally graded powder is then normally introduced into a compression mould. If the preparation of multi-coloured blanks is intended, the first process step described above is carried out several times with other colouring substances or at higher concentrations of the colouring substances, with the result that differently coloured powders are produced. In a second step these differently coloured powders are poured portionwise into a compression mould after the grading.

Compression, such as cold isostatic pressing, of a shaped body is carried out at pressures of 50 to 500 MPa, particularly preferably at 70 to 300 MPa, quite particularly preferably at 100 to 200 MPa. According to the invention a uniaxial compression is also possible.

In a further process step the obtained shaped body is sintered, in particular pre-sintered. Temperatures of 800 to 1300° C., particularly 1000° C. to 1200° C., quite particularly of 1050° C. to 1150° C., are used for this. A porous blank with a density of at least 30%, preferably 40 to 75% of the theoretical density of the oxide ceramic is obtained by the pre-sintering process. The duration of the pre-sintering at the given temperatures is 1 to 4 hours, particularly 1.5 to 2.5 hours. The complete pre-sintering step including heating and cooling processes usually lasts 38 to 72 hours.

Debindering of the shaped body takes place at the same time during the pre-sintering process. "Debindering" means the burning out of the organic constituents, in particular the binders. However, this debindering can also be carried out in a separate process step.

The obtained single- or multi-coloured blank is shaped into a dental shaped part for example in a dental laboratory or dental clinic. This can preferably take place by milling or grinding by means of a CAD/CAM unit. The thus-obtained enlarged preform of a dental shaped part of the dental restoration is then densely-sintered at a temperature of 1200° C. to 1600° C., particularly at 1300° C. to 1550° C. and quite particularly at 1400° C. to 1500° C. The duration of the dense sintering lasts between 5 minutes and 2 hours, particularly 10 to 30 minutes. The complete dense-sintering process with heating and cooling generally lasts approximately 8 hours. The milling process is carried out such that the dental shaped part displays an excess that takes into account the shrinkage of the shaped part during the dense sintering.

The dense sintering can also be carried out using microwave energy, which as a rule leads to a shortening of the process times.

The prepared dental shaped part can already represent the finished dental restoration or is processed still further, such as e.g. provided with a veneer, in order to produce the finished dental restoration.

The dental shaped parts prepared in the way described are characterized, unlike the dental shaped parts previously known from the state of the art, by a high colour homogeneity. The colouring ions are present in aqueous phase and are applied homogeneously to the surface of the oxide ceramic powders, in particular in the fluidized bed. Even at very low concentrations of about 0.001 wt.-%, relative to the total amount of powder, a homogeneous coating of the powder is obtained. It is also advantageous according to the invention that mixed colours may be obtained and blanks can in this way be prepared in multi-coloured form.

The invention contemplates the use of multi-coloured blanks of the ZrO2 ceramic, that after the dense sintering of the $ZrO_2$ ceramic there is a multi-coloured product for restorative dental medicine. This polychromatism is extremely advantageous quite particularly for multi-span bridges. Thus the natural tooth can be perfectly reproduced by such a dental restoration, as the latter does not consist of just one colour, but has a colour gradient and translucency differences as well as different colour brightnesses within the tooth. If a multi-coloured bridge according to the invention is now prepared, these aforementioned requirements or properties of a natural tooth can be easily ensured. This ease of preparation of dental shaped parts, e.g. of complicated dental restorations, such as multi-span bridges, is obtainable according to the invention by the fact that the dental technician needs to apply only a few sintered ceramic or sintered glass ceramic veneer layers, or even just one, to the multi-coloured ceramic bridge in order to achieve the most natural look. Several layers have to be applied to uncoloured ceramics as a veneer and in order to achieve special colour effects. Various sinterings are also necessary in case of single-coloured ceramics. Operations according to the invention are therefore more effective than according to the state of the art.

A further advantage is that a uniform distribution of pores is not a precondition for coloration. The infiltration technique depends on as uniform as possible a distribution of the pores in order to obtain colourings that are acceptable to at least some extent. Accordingly, wholly different colouring qualities are obtained according to the state of the art because of different roughnesses and inaccessible pores.

It is furthermore advantageous according to the invention that, with the colouring according to the invention of the oxide ceramic powders through the homogeneous distribution of the colouring substances on the surface of the powders or of the agglomerates from the primary particles of the powder, no accumulation of the colouring substances occurs. An imperfection in the structure is thereby reliably avoided. If the process described above is carried out with differently coloured oxide ceramic powders, the result after the compression, debindering and sintering is a multi-coloured blank which has a colour gradient which preferably corresponds to that of a natural tooth.

Furthermore, grain growth within the ceramic is not negatively influenced during sintering. The colour ion distribution is so favourable that neither colour gradients nor accumulations of colour ions are visible or analysable with either the human eye or with a scanning electron microscope (SEM) or a transmission electron microscope (TEM).

Finally, a process according to the invention is preferred in which the blank or the dental shaped part or the dental restoration prepared therefrom contains a composition according to the invention that is described below.

A composition according to the invention is based on $ZrO_2$, and contains the following components
  Pr, calculated as $Pr_2O_3$,
  Fe, calculated as $Fe_2O_3$,
  Tb, calculated as $Tb_2O_3$, and
  Mn, calculated as $Mn_2O_3$,
in a total quantity of 0.0001 to 0.75 wt.-%.

Surprisingly, it was shown that such a composition, despite the very small total quantity of colouring components, namely Pr, Fe, Tb and Mn, allows the preparation of blanks, dental shaped parts and finally dental restorations which are intensively coloured in the desired way in order to excellently imitate the natural tooth material.

The components Pr, Fe, Tb and Mn can be present in different oxidation stages in the composition, preferably being present in an oxidation stage other than zero.

It is assumed that during the preparation of the composition by the above-given process according to the invention, in particular after pre-sintering or dense-sintering steps have been carried out, an insertion of the components in the form of ions into the crystal lattice of the $ZrO_2$ takes place. For example, it is possible that these ions are inserted into defects of the $ZrO_2$ lattice.

The composition is therefore preferably present in sintered form. In addition it contains the given components preferably homogeneously distributed.

It is further preferred that the composition contains the components in a total quantity of 0.0001 to 0.6 and in particular 0.0004 to 0.37 wt.-%.

Furthermore, a composition which contains the components in the following quantities has proven particularly effective:

| Component | Quantities (wt.-%) |
|---|---|
| Pr, calculated as $Pr_2O_3$ | 0.0001-0.01 |
| Fe, calculated as $Fe_2O_3$ | 0.005-0.5 |
| Tb, calculated as $Tb_2O_3$ | 0.0001-0.1 |
| Mn, calculated as $Mn_2O_3$ | 0.0001-0.1 |

In addition, particular ranges also exist for the individual components as follows:

Pr, calculated as $Pr_2O_3$, in a quantity of 0.0005 to 0.01 wt.-%

Fe, calculated as $Fe_2O_3$, in a quantity of 0.005 to 0.4 wt.-%

Tb, calculated as $Tb_2O_3$, in a quantity of 0.0001 to 0.075 wt.-%

Mn, calculated as $Mn_2O_3$, in a quantity of 0.0001 to 0.075 wt.-%

Finally, it was surprisingly shown that special compositions can be very advantageously used as basic colours in the preparation of dental restorations. These are the four specially preferred embodiments described below of the composition according to the invention, giving the contained quantities of the components:

| Component | Quantities (wt.-%) |
|---|---|
| Pr, calculated as $Pr_2O_3$ | 0.001-0.003 |
| Fe, calculated as $Fe_2O_3$ | 0.005-0.04 |
| Tb, calculated as $Tb_2O_3$ | 0.0005-0.004 |
| Mn, calculated as $Mn_2O_3$ | 0.0001-0.0005 |
| Pr, calculated as $Pr_2O_3$ | 0.002-0.004 |
| Fe, calculated as $Fe_2O_3$ | 0.04-0.15 |
| Tb, calculated as $Tb_2O_3$ | 0.0005-0.004 |
| Mn, calculated as $Mn_2O_3$ | 0.0003-0.002 |
| Pr, calculated as $Pr_2O_3$ | 0.003-0.006 |
| Fe, calculated as $Fe_2O_3$ | 0.04-0.15 |
| Tb, calculated as $Tb_2O_3$ | 0.0005-0.004 |
| Mn, calculated as $Mn_2O_3$ | 0.0005-0.002 |
| Pr, calculated as $Pr_2O_3$ | 0.003-0.006 |
| Fe, calculated as $Fe_2O_3$ | 0.04-0.25 |
| Tb, calculated as $Tb_2O_3$ | 0.0005-0.004 |
| Mn, calculated as $Mn_2O_3$ | 0.001-0.007 |

Compositions according to the invention can moreover contain still further substances, such as Cr, calculated as $Cr_2O_3$, in a quantity of 0.0001 to 0.1 wt.-%.

Furthermore, it is advantageous if the composition includes a stabilizer such as $Y_2O_3$. Compositions which contain 4 to 8 wt.-% $Y_2O_3$ represent specific embodiments.

Compositions may also contain up to 1 wt.-% $Al_2O_3$. This increases the stability of the composition according to the invention under hydrothermal conditions, which is of particular importance when using the composition according to the invention as a dental material.

The composition can also contain $HfO_2$.

Compositions which contains more than 95 wt.-%, in particular more than 98 wt.-% $ZrO_2$ are contemplated. Compositions in which the $ZrO_2+HfO_2+Y_2O_3$ content of the composition is more than 95 wt.-% are also contemplated.

Compositions according to the invention is used in particular as dental material. Compositions according to the invention can in particular be prepared by a process in which a powder based on $ZrO_2$ is coated with a source of the components, such as compounds of Pr, Tb, Fe and Mn, in particular by means of fluidized bed coating.

Finally, the invention also relates to a shaped body which contains the composition according to the invention and particularly those which have a homogeneous distribution of the components Pr, Tb, Fe and Mn within the whole body and thus an excellent colour homogeneity. This shaped body is present in particular as a blank, dental shaped part or dental restoration, i.e. preferably as a sintered shaped body. The shaped body according to the invention can be produced in particular by the above-given process according to the invention for the preparation of blanks and dental shaped parts.

Blanks according to the invention can be provided with a density of 3.0 to 3.5, in particular 3.1 to 3.2 $g/cm^3$.

A shaped body is further preferred which is multi-coloured, wherein the polychromatism is brought about in particular by several differently coloured layers. Shaped bodies which have at least two differently coloured layers and preferably contain up to eight differently coloured layers have proven particularly advantageous.

The natural tooth material can be very well imitated by just such a shaped body, such as e.g. a blank, with at least three differently coloured layers. The natural tooth material can be roughly divided into three regions, namely cervical, central and incisal, each having different requirements with regard to visual appearance. Thus, the appearance of one layer is preferably matched to the cervical, and the appearance of the other two layers preferably matched to the central and incisal regions of the natural tooth. It has also proved particularly advantageous if at least one layer of the body contains a composition according to the invention and in particular a composition of the above-mentioned four special embodiments. Moreover, it is also possible that this at least one layer contains a mixture of the above-given four special embodiments and thus the basic colours represented by these embodiments can be modified.

A comparison with conventional coloured compositions based on $ZrO_2$ has shown that the special components of the compositions according to the invention, even in very small quantities, allow a sought colour intensity to be obtained. The conventional system frequently requires a much greater quantity of colouring components for this, which leads to imperfections in the structure of the bodies produced therefrom. The comparatively small quantities of colouring components used in the case of the compositions according to the invention essentially cause no imperfections in the structure of the bodies produced therefrom, with the result that they and in particular the dental restorations that are finally prepared have excellent physical properties, such as strength and chemical stability.

Finally therefore the invention also relates to the use of the composition according to the invention or of the body according to the invention for the preparation of dental restorations.

The dental restoration is in particular a crown and quite particularly preferably a bridge. It is of particular importance in particular with a bridge if the different colours present in the natural teeth that are to be replaced can be imitated as faithfully as possible. However, this is possible in an excellent way with the composition according to the invention and the shaped bodies prepared therefrom, through the provision of correspondingly differently coloured regions, such as differently coloured layers.

The invention is explained in more detail below by means of the following illustrative non-limiting examples.

EXAMPLES

All the optical values L, a and b given within the framework of the examples were determined in accordance with the standards DIN 5033 or DIN 6174, by carrying out a comparison with a white reference sample with the values $L^*=93.11$, $a^*=0.64$ and $b^*=4.22$. The value C represents the vector sum of a and b. Colour measurement was carried out by means of a Konica-Minolta CM-3700d spectrometer. The CR value was determined in accordance with the standard BS 5612 and is a measure of opacity.

Partially stabilized $ZrO_2$ powders, e.g. $TZ_{-3}Y$ or $TZ_{-3}YSB$-C, from the company Tosoh which had the compositions below were used as starting material for compositions according to the invention and shaped bodies, blanks and dental shaped parts prepared therefrom:

| | |
|---|---|
| $ZrO_2 + HfO_2 + Y_2O_3$ | >99.0 wt.-% |
| $Y_2O_3$ | 4.5-5.4 wt.-% |
| $HfO_2$ | ≤5.0 wt.-% |
| $Al_2O_3$ | 0.2-0.5 wt.-% |
| Other oxides | ≤0.5 wt.-% |
| Radioactivity | <200 Bq kg$^{-1}$ |
| Bulk density | 3.09-3.21 g cm$^{-3}$ |

An aqueous solution which contained both the colouring ions and a water-soluble binder, such as polyvinyl alcohol (e.g. Optapix PAF2 or PAF35 from the company Zschimmer & Schwarz) was used as colouring solution for the fluidized-bed coating. The colouring solution can contain one or more colouring ions in order to achieve the desired coloration after the dense sintering. The aqueous colouring solution with ca. 0.1-2 wt.-% binder (relative to the quantity of powder to be coated) contained the respective colouring ions. This solution was homogenized for approximately half an hour (magnetic stirrer or the like). This thus-prepared colouring solution was then applied completely by means of a fluidized-bed granulator on the $ZrO_2$ powder to be coated. During this step the powder to be coated was kept in suspension (fluidized bed) by means of compressed air (0.15-0.30 bar) and at the same time the colouring solution was sprayed through a nozzle, which was arranged above this fluidized bed, and applied to the powder. The spraying pressure here was between 2 to 6 bar. In addition, the compressed air which was necessary to maintain the fluidized bed was heated to approximately 30 to 80° C., and was thus able to dry the powder at the same time during the process.

Preparation of a Single-Coloured $ZrO_2$ Blank:

$ZrO_2$ powder (TZ-3YSB-C) was coated with an aqueous colouring solution based on Fe(III), Pr, Cr and Tb compounds. The thus-coloured powder was introduced into a compression mould and subjected to cold isostatic compression at ca. 200 MPa. This shaped body was then pre-sintered at a temperature of 1125° C. over a period of ca. 120 min. to produce a blank and then worked by means of CAD/CAM technology. It was then dense-sintered at ca. 1500° C. The dental shaped part had a slightly yellowish colour after the dense sintering. Square blanks were preferably prepared which preferably had the following measurements:

| | |
|---|---|
| Length | about 15 to about 60 mm |
| Width | about 10 to about 20 mm |
| Height | about 15 to about 20 mm |

The preparation of cylindrical blanks was, however, also possible. The crystallite size, analyzed by means of SEM, of the partially sintered blank was about 200 to 400 nm. The crystallite size in the densely sintered restoration was about 400 to 800 nm.

The following TABLE 1 gives the compositions of differently coloured blanks according to Examples 1 to 10 together with the optical values after the dense sintering. The levels of the components are expressed as levels of the respective trivalent oxide. $ZrO_2$ powders from Tosoh, Japan, containing 4-8 wt.-% $Y_2O_3$ were used as starting material. The powders differed in their primary particle size, specific surface and binder content. These powders were provided as described above with the colouring components.

TABLE 1

| Example | Composition (TZ-3Y, TZ-3YSB or TZ-3YSB-E) + following components | L* | a* | b* | C* | CR | Optical appearence |
|---|---|---|---|---|---|---|---|
| 1 | 0.05 wt.-% $Pr_2O_3$<br>0.0001 wt.-% $Cr_2O_3$<br>0.001 wt.-% $Fe_2O_3$<br>0.0001 wt.-% $Tb_2O_3$ | 84.02 | 2.37 | 25.74 | 25.85 | 94.33 | yellowish |
| 2 | 0.1 wt.-% $Cr_2O_3$<br>0.0001 wt.-% $Tb_2O_3$<br>0.0001 wt.-% $Pr_2O_3$<br>0.001 wt.-% $Fe_2O_3$ | 63.30 | 1.78 | 5.22 | 5.51 | 98.10 | dark grey |
| 3 | 0.1 wt.-% $Fe_2O_3$<br>0.0001 wt.-% $Cr_2O_3$<br>0.0001 wt.-% $Pr_2O_3$<br>0.0001 wt.-% $Tb_2O_3$ | 81.39 | 1.80 | 17.23 | 17.33 | 97.97 | reddish-brown |

TABLE 1-continued

| Example | Composition (TZ-3Y, TZ-3YSB or TZ-3YSB-E) + following components | L* | a* | b* | C* | CR | Optical appearence |
|---|---|---|---|---|---|---|---|
| 4 | 0.072 wt.-% $Fe_2O_3$<br>0.003 wt.-% $Cr_2O_3$<br>0.003 wt.-% $Pr_2O_3$<br>0.0001 wt.-% $Tb_2O_3$ | 79.19 | 1.87 | 18.64 | 18.74 | 99.47 | reddish-brown (tooth colour) |
| 5 | 0.0001 wt.-% $Pr_2O_3$<br>0.0001 wt.-% $Mn_2O_3$<br>0.0001 wt.-% $Fe_2O_3$<br>0.05 wt.-% $Tb_2O_3$ | 84.23 | 1.61 | 22.95 | 23.00 | 96.07 | yellowish |
| 6 | 0.0001 wt.-% $Pr_2O_3$<br>0.1 wt.-% $Mn_2O_3$<br>0.0001 wt.-% $Fe_2O_3$<br>0.0001 wt.-% $Tb_2O_3$ | 51.48 | 2.49 | −1.71 | 3.02 | 95.02 | anthracite |
| 7 | 0.0040 wt.-% $Pr_2O_3$<br>0.0001 wt.-% $Mn_2O_3$<br>0.001 wt.-% $Fe_2O_3$<br>0.0001 wt.-% $Tb_2O_3$ | 86.87 | −0.52 | 10.40 | 40.42 | 92.49 | slightly yellowish |
| 8 | 0.001 wt.-% $Pr_2O_3$<br>0.0001 wt.-% $Mn_2O_3$<br>0.5 wt.-% $Fe_2O_3$<br>0.0001 wt.-% $Tb_2O_3$ | 72.24 | 6.10 | 22.10 | 22.92 | 98.59 | yellow-brown |
| 9 | 0.0006 wt.-% $Pr_2O_3$<br>0.0001 wt.-% $Mn_2O_3$<br>0.0002 wt.-% $Fe_2O_3$<br>0.0001 wt.-% $Tb_2O_3$ | 89.94 | −0.20 | 5.05 | 5.05 | 96.70 | cream-white |
| 10 | 0.05 wt.-% $Pr_2O_3$<br>0.1 wt.-% $Mn_2O_3$<br>0.5 wt.-% $Fe_2O_3$<br>0.05 wt.-% $Tb_2O_3$ | 53.09 | 1.54 | 4.35 | 4.62 | 99.49 | anthracite |

Example 11

Preparation of a Multi-Coloured Blank Based on $ZrO_2$

Differently coloured powders (different tooth colours) were homogeneously poured successively into a compression mould according to the desired layer thickness and colour transition. The powder was subjected to cold isostatic compression at approximately 200 MPa and then pre-sintered at 1125° C. for about 120 min. A preform of a dental shaped part was then produced from the blank and dense-sintered. The dental shaped part was then cut open lengthwise, and a colour gradient was seen which cannot be thus prepared by means of the infiltration technique. This natural colour gradient, thus the reproduction of the visual properties of the natural tooth, became clear in particular in the case of a 3-span side-tooth bridge. Using the blank according to the invention, it proved possible to reconstruct the natural colour transition without an additional coating technique in the dense-sintered dental shaped part. The colour transition of a side-tooth bridge according to the invention is characterized in that a higher chroma (a more intense colour) is realized in the fissure and at the neck of the tooth than in the area of the cusps of the tooth. A much better aesthetic was thus obtained compared with the substances and materials of the state of the art. Furthermore, the time spent by the dental technician on the preparation of the completely coated restoration was able to be reduced.

Aqueous systems with soluble ionogenic compounds, preferably chlorides and nitrates, were used as colouring solutions.

Blanks with a colour transition comprising e.g. 2 up to 10 colours were able to be produced in a large homogeneity as single- and multi-coloured blanks with this process.

Example 12

Comparative Example According to the State of the Art

A 3-span bridge framework was ground from an IPS e.max ZirCAD® bridge block in a CAD/CAM unit (Sirona in Lab®). The shrinkage factor of approximately 20% per space axis was taken into account by a corresponding enlargement ratio during grinding. The grinding process was carried out wet, with the result that the framework had to be dried before the infiltration process. The drying was carried out over 2 hours at about. 80° C. under an infrared lamp. The reworked frameworks (removal of handpiece and regrinding of the edges) were infiltrated with the following solutions for the colouring (values in wt.-%), in order to ascertain differences in the colour homogeneity:

TABLE 2

| Solution | $Fe(NO_3)_3*_9H_2O$ | $H_2O$ | PEG 20000 | Ethanol |
|---|---|---|---|---|
| 1 | 4.2 | 76.6 | — | 19.2 |
| 2 | 4.8 | 54.4 | 27.2 | 13.6 |

PEG 20000: Polyethylene glycol (Fluka, Buchs, Switzerland)

A bridge framework was immersed for 2 min. in solution 1, infiltration taking place by capillary action. The use of a vacuum or above-atmospheric pressure was dispensed with. After the infiltration the framework was removed from the solution and dabbed dry by means of a paper towel in order to remove the excess colouring solution from the surface. The drying followed under an infrared lamp at 80° C. for approximately 2 hours. Already at this point in time a concentration of the Fe ions at exposed points of the framework (e.g. framework cusps of the masticating surface, high surface curvature) revealed itself. Even after the dense sintering at 1500° C. for 30 min. the colour inhomogeneity resulting therefrom was clearly visible. A uniform outer colouring was not realizable.

A further bridge framework was dipped into colouring solution 2 for 2 min. to improve the colour homogeneity. Post-treatment took place as described above. It was shown that the disadvantage of the superficial colour inhomogeneity was able to be dealt with by the addition of the organic component and thus an increase in the viscosity of the colouring solution. The sintering also took place as described above. However, after the bridge framework was sectioned along the longitudinal axis it was shown that the colouring had taken place only in the outer layer zone of about 0.6 to 1.0 mm and thus there was no homogeneous colouring within the whole framework. This is possibly sufficient for an abutment crown, but there are major doubts in the area of the connectors and of the intermediate section of the bridge. During a subsequent grinding by the dental technician there is the danger that uncoloured areas will be partially exposed and the originally intended effect of a colouring will be lost.

The comparative example shows that when infiltration is used as a colouring process only a superficial colouring can be achieved or a complete thorough colouring is achieved with only inhomogeneous colouring varying locally in strength (concentration of the colour ions). These disadvantages are avoided according to the invention. A homogeneous colouring of the whole blank is always to be recorded.

It has also proved advantageous if nanoscale $ZrO_2$ powder is used as starting material (primary particle size between 5 and 50 nm and a specific surface of >100 $m^2 \cdot g^{-1}$) for the preparation of the blocks. After working to produce a bridge framework this shows a clearly reduced temperature during the dense sintering. Thus, depending on the materials used, temperatures of below 1250° C. were reached, which allows a dense sintering in customary dental firing furnaces. To prepare coloured blocks (single- and multi-coloured) the coloured powders used above were added as a so-called colour concentrate to the nanoscale $ZrO_2$ powder in a proportion of 0.0001 to 2.0 wt.-%. A temperature change during the dense sintering is not necessary.

Examples 13 to 17

Further particularly preferred compositions according to the invention were prepared in the manner given above for Examples 1 to 10 and further processed into blanks, dental shaped parts and dental restorations. The portions of the components, calculated as the respective trivalent oxide, and also the total portion of these colour components and the presence of an additive possibly present during the compression into shaped bodies are listed in Table 3 below. The portions are given as mg of component per kg of the whole composition.

The surfactant was polyglycol ether or alkyl sulphonates.

These compositions and in particular those according to Examples 13 and 17 can be used as typical dental colours. Surprisingly, despite the very small quantities of colouring components, these compositions can be processed into intensely coloured dental restorations, such as in particular crowns and bridges.

The optical properties of coloured dense-sintered blanks prepared from them are listed in Table 4 below.

TABLE 3

| Example | $Fe_2O_3$ mg/kg | $Pr_2O_3$ mg/kg | $Tb_2O_3$ mg/kg | $Mn_2O_3$ mg/kg | Total portion colour comp. mg/kg | Additives |
|---|---|---|---|---|---|---|
| 13 | 329 | 15 | 7 | 1 | 352 | Optapix PAF35 |
| 14 | 1 | 1 | 1 | 1000 | 1003 | Surfactant |
| 15 | 5000 | 10 | 1 | 1 | 5012 | Surfactant |
| 16 | 1 | 1 | 500 | 1 | 503 | Surfactant |
| 17 | 1000 | 25 | 6 | 10 | 1041 | Surfactant |

TABLE 4

| Example | L | A | b | C | CR |
|---|---|---|---|---|---|
| 13 | 87.76 | −1.02 | 10.22 | — | 94.62 |
| 14 | 51.48 | 2.49 | −1.71 | 3.02 | 95.02 |
| 15 | 72.24 | 6.10 | 22.10 | 22.92 | 98.59 |
| 16 | 84.23 | 1.61 | 22.95 | 23.00 | 96.07 |
| 17 | 82.15 | 0.48 | 13.60 | — | 99.72 |

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. A composition comprising $ZrO_2$, the composition further comprising the following components in wt.-%:

| | |
|---|---|
| Pr, calculated as $Pr_2O_3$ | 0.001-0.003 |
| Fe, calculated as $Fe_2O_3$ | 0.005-0.04 |
| Tb, calculated as $Tb_2O_3$ | 0.0005-0.004 |
| Mn, calculated as $Mn_2O_3$ | 0.0001-0.0005. |

2. A composition comprising $ZrO_2$, the composition further comprising the following components in wt.-%:

| | |
|---|---|
| Pr, calculated as $Pr_2O_3$ | 0.002-0.004 |
| Fe, calculated as $Fe_2O_3$ | 0.04-0.15 |
| Tb, calculated as $Tb_2O_3$ | 0.0005-0.004 |
| Mn, calculated as $Mn_2O_3$ | 0.0003-0.002. |

3. A composition comprising $ZrO_2$, the composition further comprising the following components in wt.-%:

| | |
|---|---|
| Pr, calculated as $Pr_2O_3$ | 0.003-0.006 |
| Fe, calculated as $Fe_2O_3$ | 0.04-0.15 |
| Tb, calculated as $Tb_2O_3$ | 0.0005-0.004 |
| Mn, calculated as $Mn_2O_3$ | 0.0005-0.002. |

4. A composition comprising $ZrO_2$, the composition further comprising the following components in wt.-%:

| | |
|---|---|
| Pr, calculated as $Pr_2O_3$ | 0.003-0.006 |
| Fe, calculated as $Fe_2O_3$ | 0.04-0.25 |
| Tb, calculated as $Tb_2O_3$ | 0.0005-0.004 |
| Mn, calculated as $Mn_2O_3$ | 0.001-0.007. |

5. A multi-colored shaped body comprising a composition comprising $ZrO_2$ and further comprising the following components:
Pr, calculated as $Pr_2O_3$,
Fe, calculated as $Fe_2O_3$,
Tb, calculated as $Tb_2O_3$, and
Mn, calculated as $Mn_2O_3$,
in a total quantity of 0.0001 to 0.75 wt.-%,
wherein the multi-coloration is produced by differently colored layers.

6. The shaped body according to claim 5, wherein said composition comprises
Tb, calculated as $Tb_2O_3$, in a quantity of 0.0001 to 0.075 wt.-% and.

7. The shaped body according to claim 6, wherein said composition comprises the components in a total quantity of 0.0001 to 0.6 wt.-%.

8. The shaped body according to claim 7, wherein said composition comprises the components in a total quantity of 0.0004 to 0.37 wt.-%.

9. The shaped body according to claim 6, wherein said composition comprises the components in the following quantities, in wt.-%:

| | |
|---|---|
| Pr, calculated as $Pr_2O_3$ | 0.0001-0.01 |
| Fe, calculated as $Fe_2O_3$ | 0.005-0.5 |
| Tb, calculated as $Tb_2O_3$ | 0.0001-0.1 |
| Mn, calculated as $Mn_2O_3$ | 0.0001-0.1. |

10. The shaped body according to claim 6, wherein said composition comprises Pr, calculated as $Pr_2O_3$, in a quantity of 0.0005 to 0.01 wt.-%.

11. The shaped body according to claim 6, wherein said composition comprises Fe, calculated as $Fe_2O_3$, in a quantity of 0.0005 to 0.4 wt.-%.

12. The shaped body according to claim 6, wherein said composition comprises Fe, calculated as $Mn_2O_3$, in a quantity of 0.0001 to 0.075 wt.-%.

13. The shaped body according to claim 6, wherein said composition comprises 4 to 8 wt.-% $Y_2O_3$.

14. The shaped body according to claim 6, wherein said composition comprises up to 1 wt.-% $Al_2O_3$.

15. The shaped body according to claim 6, wherein said composition is a powder composition and comprises 98.0 to 99.9999 wt.-% of nanoscale $ZrO_2$ powder.

16. The shaped body according to claim 15, wherein the nanoscale $ZrO_2$ powder has a specific surface area of ≥100 m2*g-1.

17. The shaped body according to claim 15, wherein the nanoscale $ZrO_2$ powder has a primary particle size between 5 and 50 nm.

18. The shaped body according to claim 6, wherein said composition is obtainable by a process in which a powder based on $ZrO_2$ is coated with compounds of Pr, Tb, Fe and/or Mn.

19. The shaped body according to claim 18, wherein the powder is coated by means of fluidized bed coating.

20. The shaped body according to claim 6, wherein the shaped body is in the form of a blank, dental shaped part or dental restoration.

21. The shaped body according to claim 6, wherein the shaped body comprises at least 2 differently colored layers.

22. The shaped body according to claim 21, wherein the shaped body comprises up to 8 differently colored layers.

23. The shaped body according to claim 21, wherein at least one layer has the composition according to claim 1.

24. The shaped body according to claim 21, wherein at least one layer has a composition comprising $ZrO_2$, the composition further comprising the following components in wt.-%:

| | |
|---|---|
| Pr, calculated as $Pr_2O_3$ | 0.001-0.003 |
| Fe, calculated as $Fe_2O_3$ | 0.005-0.04 |
| Tb, calculated as $Tb_2O_3$ | 0.0005-0.004 |
| Mn, calculated as $Mn_2O_3$ | 0.0001-0.0005. |

25. A dental restoration comprising the shaped body according to claim 21.

26. The dental restoration according to claim 25, wherein the dental restoration is in the form of a crown or a bridge.

27. A single- or multi-colored body made from colored oxide ceramic powder having a ratio of oxide ceramic component to mixtures of coloring oxides, of 100: 0.0001 to 2.0 parts by weight, wherein $Pr_2O_3$, $Fe_2O_3$, $Tb_2O_3$ and $Cr_2O_3$ are used as coloring oxides and wherein $Tb_2O_3$ is used in a quantity of 0.0001 to 0.075 wt. %.

28. The single- or multi-colored body according to claim 27, wherein the coloring oxides are selected from the oxides of the d- and f-elements of the periodic table.

29. The single- or multi-colored body according to claim 28, wherein oxides of V, Ti, Nd, Eu, Dy, Er and/or Yb are used as further coloring oxides.

30. A dental restoration part comprising the shaped body according to claim 21.

31. A single- or multi-colored body made from colored oxide ceramic powder having a ratio of oxide ceramic component to mixtures of coloring oxides, of 100: 0.0001 to 2.0 parts by weight, wherein $Pr_2O_3$, $Fe_2O_3$, $Tb_2O_3$ and $Mn_2O_3$ are used as coloring oxides, wherein the coloring oxides are used in the following quantities, in wt.-%:

| | |
|---|---|
| Pr, calculated as $Pr_2O_3$ | 0.001-0.003 |
| Fe, calculated as $Fe_2O_3$ | 0.005-0.04 |
| Tb, calculated as $Tb_2O_3$ | 0.0005-0.004 |
| Mn, calculated as $Mn_2O_3$ | 0.0001-0.0005. |

32. A single- or multi-colored body made from colored oxide ceramic powder having a ratio of oxide ceramic component to mixtures of coloring oxides, of 100: 0.0001 to 2.0 parts by weight, wherein $Pr_2O_3$, $Fe_2O_3$, $Tb_2O_3$ and $Mn_2O_3$ are used as coloring oxides, wherein the coloring oxides are used in the following quantities, in wt.-%:

| | |
|---|---|
| Pr, calculated as $Pr_2O_3$ | 0.002-0.004 |
| Fe, calculated as $Fe_2O_3$ | 0.04-0.15 |
| Tb, calculated as $Tb_2O_3$ | 0.0005-0.004 |
| Mn, calculated as $Mn_2O_3$ | 0.0003-0.002. |

33. A single- or multi-colored body made from colored oxide ceramic powder having a ratio of oxide ceramic component to mixtures of coloring oxides, of 100: 0.0001 to 2.0 parts by weight, wherein $Pr_2O_3$, $Fe_2O_3$, $Tb_2O_3$ and $Mn_2O_3$ are used as coloring oxides, wherein the coloring oxides are used in the following quantities, in wt.-%:

| | |
|---|---|
| Pr, calculated as $Pr_2O_3$ | 0.003-0.006 |
| Fe, calculated as $Fe_2O_3$ | 0.04-0.15 |
| Tb, calculated as $Tb_2O_3$ | 0.0005-0.004 |
| Mn, calculated as $Mn_2O_3$ | 0.0005-0.002. |

34. A single- or multi-colored body made from colored oxide ceramic powder having a ratio of oxide ceramic component to mixtures of coloring oxides, of 100: 0.0001 to 2.0 parts by weight, wherein $Pr_2O_3$, $Fe_2O_3$, $Tb_2O_3$ and $Mn_2O_3$ are used as coloring oxides, wherein the coloring oxides are used in the following quantities, in wt.-%:

| | |
|---|---|
| Pr, calculated as $Pr_2O_3$ | 0.003-0.006 |
| Fe, calculated as $Fe_2O_3$ | 0.04-0.25 |
| Tb, calculated as $Tb_2O_3$ | 0.0005-0.004 |
| Mn, calculated as $Mn_2O_3$ | 0.001-0.007. |

35. The shaped body according to claim 5, wherein the shaped body is in the form of a blank, dental shaped part or dental restoration.

36. The shaped body according to claim 5, wherein the shaped body comprises at least 2 differently colored layers.

37. The shaped body according to claim 36, wherein the shaped body comprises up to 8 differently colored layers.

38. A dental restoration comprising the shaped body according to claim 5.

39. The dental restoration according to claim 38, wherein the dental restoration is in the form of a crown or a bridge.

* * * * *